United States Patent [19]

Schwierz et al.

[11] Patent Number: 4,962,513

[45] Date of Patent: Oct. 9, 1990

[54] COMPUTER TOMOGRAPHY APPARATUS WHICH AVOIDS IMAGE ARTIFACTS CAUSED BY PERIODICAL VOLTAGE VARIATIONS

[75] Inventors: Guenter Schwierz, Neunkirchen; Joachim Kestler, Pinzberg, both of Fed. Rep. of Germany

[73] Assignee: Siemens Aktiengesellschaft, Berlin and Munich, Fed. Rep. of Germany

[21] Appl. No.: 430,369

[22] Filed: Nov. 2, 1989

[30] Foreign Application Priority Data

Nov. 22, 1988 [EP] European Pat. Off. ........ 88119417.9

[51] Int. Cl.$^5$ .......................... A61B 6/00; H01J 35/14
[52] U.S. Cl. ........................................ 378/12; 378/12; 378/19; 378/138
[58] Field of Search ................. 378/4, 12, 19, 91, 136, 378/138, 145

[56] References Cited

U.S. PATENT DOCUMENTS

| | | | |
|---|---|---|---|
| 4,041,315 | 8/1977 | Hounsfield | 378/11 |
| 4,130,759 | 12/1978 | Haimson | |
| 4,352,021 | 9/1982 | Boyd et al. | 378/12 |
| 4,485,480 | 11/1984 | Kohno et al. | 378/19 |
| 4,597,094 | 6/1986 | Kleinman | 378/95 |
| 4,754,468 | 6/1988 | Mori | 378/19 |
| 4,837,792 | 6/1989 | Goethert | 378/4 |
| 4,916,718 | 4/1990 | Manring | 378/15 |

OTHER PUBLICATIONS

"High-Speed Computed Tomography: Systems and Performance", Peschmann et al., Applied Optics, vol. 24, No. 3, Dec. 1, 1985 (pp.4052-4060).

Primary Examiner—Janice A. Howell
Assistant Examiner—Kim-Kwok Chu
Attorney, Agent, or Firm—Hill, Van Santen, Steadman & Simpson

[57] ABSTRACT

A computer tomography apparatus has a circular anode and a circular radiation detector in which a patient to be examined is disposed. An electron beam from an electron gun is deflected by a beam deflection system, fed by a line voltage, so that the focus of the electron beam on the anode orbits the patient, thereby irradiating the patient from different angular positions. The radiation attenuated by the patient is recorded by the radiation detector, and corresponding electrical signals are read-out from the radiation detector by a data acquisition system, from which an image of the patient is constructed. To avoid image artifacts due to fluctuations such as ripples in the line voltage which supplies the tomography apparatus, the beam deflection system and the data acquisition system are synchronized so that, at each of n revolutions of the focus, the focus movement and the read-out of the measured values ensue slightly phase-shifted compared to the preceding revolution relative to the ripple period of the line voltage.

6 Claims, 2 Drawing Sheets

COMPUTER TOMOGRAPHY APPARATUS WHICH AVOIDS IMAGE ARTIFACTS CAUSED BY PERIODICAL VOLTAGE VARIATIONS

BACKGROUND OF THE INVENTION

1. Field of the Invention

The present invention is directed to a computer tomography apparatus of the type having a circular anode and a circular radiation detector surrounding a measuring opening in which a patient to be examined is disposed so that the patient is irradiated with x-radiation from different angular positions.

2. Description of the Prior Art

Computer tomography devices are known in the art wherein a patient is disposed inside of a circular anode and a circular radiation detector. An electron beam is generated and is deflected by a beam deflection system in a circular orbit, on the circular anode, around the patient, so that the patient is irradiated by a fan-shaped x-ray beam from different angular directions. The radiation attenuated by the patient is recorded by the radiation detector, consisting of an array of individual detector elements, and the measured values from the detector elements are supplied to a data acquisition system, from which the measured values are supplied to a computer which constructs an image of a slice of the examination subject from those values. The image is then visually displayed.

Other types of computer tomography devices are known wherein the x-ray source and the radiation detector are mechanically moved around the examination subject, so as to expose the patient to radiation from the different angular positions. In tomography devices of this type, if a tomogram of a beating heart is needed, measured values of the attenuated radiation during a plurality of heart cycles must be selected in order to achieve images of the beating heart which are low in artifacts. The measured values are always produced at the same heart phase, i.e., at the same time within the heart beat cycle. Fluctuations in the line voltage which supplies high-voltage generator for the x-ray source will result in variations of the intensity and mean energy of the x-radiation and in migrations of the x-ray beam position as it exits the x-ray source. Beam position monitors in this type of tomography apparatus can be mechanically mounted at the beam exit port of the x-ray source, and thus co-moved with the x-ray source around the patient. The detector then supplies a signal to the computer which is used to correct for voltage variations, so that the change in the intensity and mean energy of the x-ray beam caused by the voltage fluctuations can be taken into account in the computerized construction of the image, and image artifacts, which would otherwise be caused by this voltage fluctuation, can be avoided.

A computer tomography apparatus of the type first described above, i.e., having a circular anode on which an electron beam orbits around a patient, is described in U.S. Pat. No. 4,352,021. In this type of computer tomography apparatus, a very fast movement of the focus around the circular anode is possible, so that the registration of heart phases is possible during a single heart cycle. The focus of the electron beam is conducted around the circular anode using an electrical and/or magnetic beam deflection system. Therefore mechanical parts for moving the focus are not present in this type of tomography apparatus, and the aforementioned mechanical radiation monitors cannot be used, and thus image artifacts caused by fluctuations in the line voltage are present.

SUMMARY OF THE INVENTION

It is an object of the present invention to provide a computer tomography apparatus of the type having a circular anode on which an electron beam is caused to orbit an examination subject, wherein line voltage fluctuations do not lead to image artifacts.

The above object is achieved in accordance with the principles of the present invention in a computer tomography apparatus, and a method for operating such an apparatus, wherein the beam deflection system and the data acquisition system are synchronized so that, at each of the n revolutions of the focus around the patient, the focus movement and the read-out of the measured values ensue slightly phase-shifted compared to the preceding resolution relative to the ripple of the line voltage which is supplied to the deflection voltage generator which supplies the electron beam deflection unit. Such synchronization is based on two assumptions. The first assumption is that the fluctuation of the line voltage is of the type known as voltage ripple, and occurs substantially periodically, with the ripple frequency being a known multiple of the line frequency. The second assumption is that the focus must repeatedly sweep or orbit the circular anode in order to achieve low-noise images.

In the apparatus and method disclosed and claimed herein, it is thus irrelevant whether homologous measured data are combined before the image construction, or whether tomography images respectively associated with the individual revolutions of the focus are superimposed.

DESCRIPTION OF THE PREFERRED EMBODIMENTS

Figure 1:
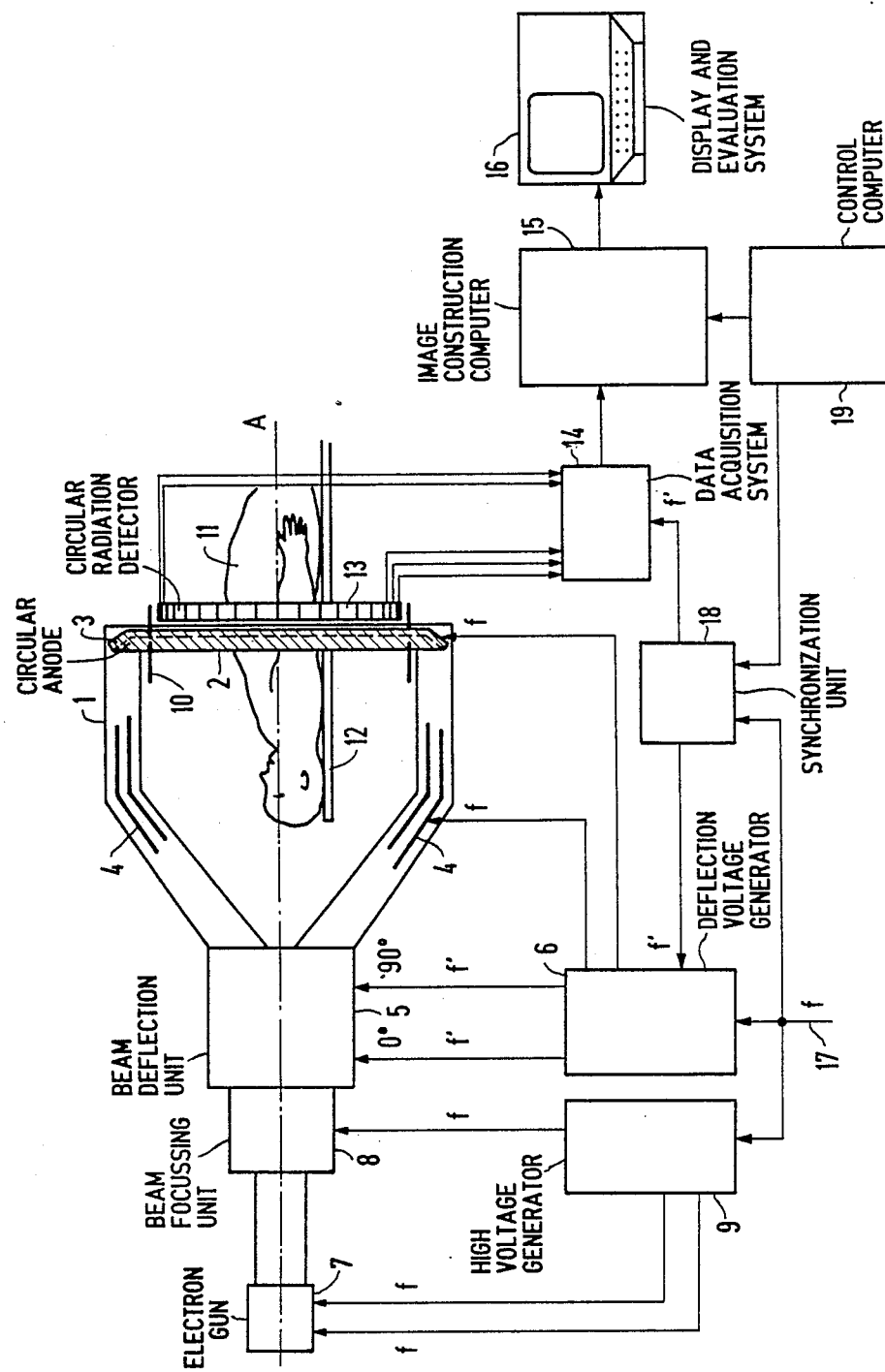
FIG. 1 is a schematic block diagram of a computer tomography apparatus constructed in accordance with the principles of the present invention.

A computer tomography apparatus constructed in accordance with the principles of the present invention is shown in FIG. 1, and includes a vacuum vessel 1 of known construction which includes a circular anode 3. The volume surrounded by the anode 3 defines a measuring aperture 2. An electron gun 7 generates an electron beam which is focussed in a beam focusing unit 8. Both the electron gun 7 and the beam focusing unit 8 are supplied with high voltage from a high voltage generator 9. The focussed beam is deflected in a beam deflection unit 5 so as to enter into the vacuum vessel 1 in which further deflection plates 4 are disposed. The beam deflection unit 5 is fed by a deflection voltage generator 17. The focus of the electron beam on the circular anode 3 is caused to orbit around the measuring aperture 2 by the beam deflection unit 5. The electron gun 7, the beam focusing unit 8, the beam deflection unit 5, the vacuum vessel 1 with the deflection plates 4 therein, and the anode 3 thus constitute an x-ray source.

The focus rotating around the circular anode 3 generates a fan-shaped rotating x-ray beam, which may be gated by a diaphragm 10. The fan-shaped x-ray beam transirradiates a patient 11, lying on a patient support 12 in the measuring aperture 2, from different directions as the electron beam focus orbits or revolves around the aperture 2. The radiation attenuated by the patient 11 is incident on a circular radiation detector 13, also surrounding the measuring aperture 2, which consists of a circular row of individual detector elements. The x-ray beam proceeds at an angle relative to the axis A which deviates from 90°. The detector elements measure the incident radiation, and each supplies an electrical signal corresponding to the incident radiation as a measured value to a data acquisition system 14 which conducts a read-out of each detector element. The signals from the data acquisition system 14 are supplied to an image construction computer 15, which calculates the attenuation values of predetermined points of the examined slice of the patient 11 in a known manner, and generates an image which can be displayed on a display and evaluation system 16.

Each of the high voltage generator 9 and the deflection voltage generator 6 are supplied by the line voltage on line 17. The line voltage may exhibit a fluctuation in the form of a ripple which, if present will be at a frequency (and thus have a period) which is a known multiple of the line frequency. The line voltage is also supplied to a synchronization unit 18, which identifies the frequency of the line voltage and supplies signals based thereon to each of the deflection system 6 and the data acquisition system 14 so that, at each of the n revolutions of the focus, the focus movement and the read-out of the measured values ensue slightly phase-shifted compared to the preceding revolution relative to the ripple period of the high-voltage of the x-ray source, which is derived from the line frequency. For this purpose, a control computer 19 is connected to the synchronization unit 18 and to the computer 15.

The phase offset is selected as the p-fold multiple of the $n^{th}$ part of the ripple period. The number n denotes the plurality of focus revolutions which are used, and p denotes an arbitrary integer. The number p is preferably selected such that p and n are relatively prime. The effectiveness of this method can be recognized in the following way.

Let rl (ft) reference the ripple function supplied by the high-voltage generator 9 having a ripple frequency f and the chronological variable t. The Fourier development is as follows:

$$rl\,(ft) = \sum_{m=-\infty}^{+\infty} a_m \exp{(j2\pi m ft)}.$$

By averaging rl (ft) over n sampling points equidistantly distributed in the chronological spacing $$\Delta t = p/(n \cdot f),$$

the reduced ripple function rn (ft) is derived as follows:

$$\begin{aligned} rn\,(ft) &= (1/n) \sum_{k=0}^{n-1} rl\,(f \times (t + k \cdot \Delta t)) \\ &= \sum_{m=-\infty}^{+\infty} a_m \left( 1/n \sum_{k=0}^{n-1} \exp(j2\pi kpm/n) \right) \exp(j2\pi m ft) \\ &= \sum_{m=-\infty}^{+\infty} a_{m \cdot n'} \exp(j2\pi \cdot n' ft). \end{aligned}$$

In the above, $n'=n/q$, with q being the highest common divisor of p and n. Only those harmonics having an index which is a whole multiple of $n'$ are not suppressed by the averaging. The most favorable relationships are present when $n=n'$, i.e., when n and p are relatively prime.

The revolution time tu of the focus, the number n of revolutions, and the integer p are selected such that $$tu = (l+p/n)tr$$

is valid with l being an integer.

As an example, for a low-frequency high-voltage generator 9, tr=10 ms can apply. If l=5 and p=1 are selected, and n is selected between 10 and 20, it follows that $$tu = (5 + 1/n)tr \approx 50 \text{ ms}.$$

The condition $$tu = (l+p/n)tr$$

can be observed by frequency synchronization. With f'=1/tu as the revolution frequency, $$f' = f/(l+p/n)$$

is to be set.

The rated phase which is characterized by the integers l, p and n is prescribed by the central control computer 15. The synchronization 18 supplies the frequency f' which is required for guiding the electron beam on the specified circle and for the read-out clock at the detector elements. All voltages and currents are subject to fluctuations having the frequency f, as identified in FIG. 1.

Figure 2:
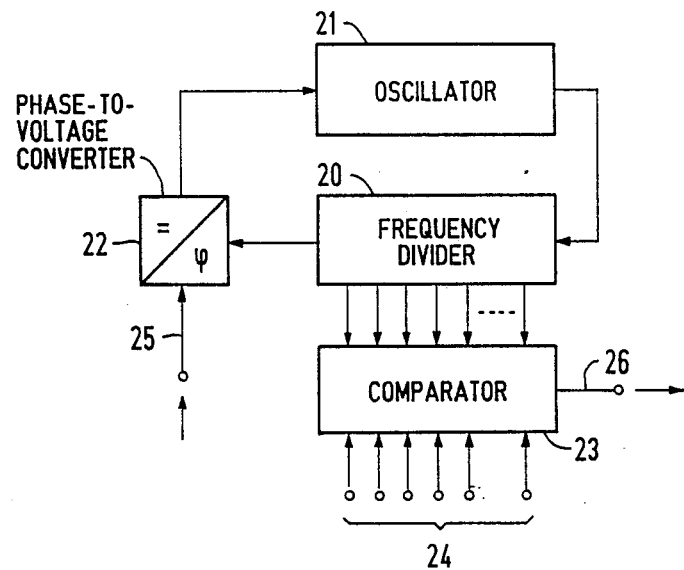
FIG. 2 is a schematic block diagram for an exemplary embodiment of the synchronization unit in the apparatus of FIG. 1.

A block circuit diagram for an embodiment of the synchronization unit 18 is shown in FIG. 2. This embodiment includes a frequency divider 20, an oscillator 21, a phase-to-voltage converter 22, and a comparator 23 having an input 24 to which information identifying the rated phase is supplied. The phase-to-voltage converter 22 has an input 25 to which the line frequency is supplied, and an output 26.

Continuing with the above example, if the line frequency is selected as 50 Hz, and if the frequency divider 20 has a division ratio of 1024:1, the oscillator frequency will be fixed at 51.2 kHz. A line frequency of 60 Hz, and other division ratios, are also possible. The synchronization unit 18 supplied the frequency f' for the deflection voltage generator 6 and for the data acquisition system 14.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computer tomography apparatus comprising:
   an x-radiator including means for generating a focussed electron beam, a circular anode on which said focussed electron beam is incident at a focus so as to produce a fan-shaped x-ray beam, said circular anode having a central opening defining an examination aperture, and an electron beam deflection means for moving said focus around said circular anode in a plurality of revolutions so that said x-ray beam irradiates said examination aperture from a plurality of different angular directions so as to irradiate a slice of an examination subject, said electron beam deflection means being supplied with a line voltage having a ripple of known periodicity;
   means adapted for supporting said examination subject in said examination aperture;
   detector means, consisting of a plurality of sideside detector elements arranged in a circle surrounding said examination aperture, for detecting x-radiation attenuated by said examination subject and generating electrical signals corresponding to the detected radiation;
   data acquisition means connected to said detector means for reading out said electrical signals from each of said detector elements;
   means connected to said data acquisition means for constructing an image of said irradiated slice of said examination subject from said electrical signals; and
   synchronization means connected to said electron beam deflection means and to said data acquisition system for, for each revolution of said focus on said circular anode, phase-shifting the focus movement and the read-out of said detector elements, compared to a preceding revolution of said focus, relative to the ripple period of said line voltage.

2. A computer tomography apparatus as claimed in claim 1, wherein said synchronization means is a means for phase-shifting the focus movement and the read-out of said detector elements by a p-fold multiple of the $n^{th}$ part of the ripple period, wherein p is an integer and n is the number of revolutions of said electron beam focus around said circular anode.

3. A computer tomography apparatus as claimed in claim 1, wherein said synchronization means is a means for phase-shifting the focus movement and the read-out of said detector elements by a p-fold multiple of the $n^{th}$ part of the ripple period, wherein p is an integer and n is the number of revolutions of said electron beam focus around said circular anode, and wherein p and n are relatively prime.

4. A method for operating a computer tomography apparatus comprising the steps of:
   generating a fan-shaped x-ray beam by focusing an electron beam on a circular anode having an opening defining an examination aperture;
   deflecting said electron beam around said circular anode in a plurality of revolutions to irradiate a slice of an examination subject disposed in said examination aperture by said electron beam from a plurality of different angular directions;
   supplying a voltage to deflect said electron beam derived from a line voltage, said line voltage having a ripple of known periodicity;
   detecting radiation attenuated by said examination subject using a plurality of side-by-side detector elements arranged in a circle surrounding said examination aperture and generating electrical signals corresponding to the detected radiation;
   reading-out said electrical signals from said detector elements;
   constructing an image of said irradiated slice of said examination subject from said electrically signals; and
   synchronizing, for each revolution of said electron beam around said circular anode, the revolution of said electron beam around said circular anode and the read-out of said detector elements by phase-shifting the electron beam movement and the read-out of said detector elements compared to a preceding revolution of said electron beam relative to the ripple period of said line voltage.

5. A method as claimed in claim 4, wherein the step of synchronizing is further defined by phase-shifting the electron beam movement and the read-out of said detector elements by a p-fold multiple of the $n^{th}$ part of the ripple period, wherein the p is an integer and n is the number of revolutions of said electron beam around said circular anode.

6. A method as claimed in claim 4, wherein the step of synchronizing is further defined by phase-shifting the electron beam movement and the read-out of said detector elements by a p-fold multiple of the $n^{th}$ part of the ripple period, wherein the p is an integer and n is the number of revolutions of said electron beam focus around said circular anode, and wherein p and n are relatively prime.

* * * * *